United States Patent
Dawes et al.

[11] 3,956,306
[45] *May 11, 1976

[54] TRIAZOLYLTHIOPHOSPHORIC ACID ESTERS

[75] Inventors: Dag Dawes, Pratteln; Beat Bohner, Binningen, both of Switzerland

[73] Assignee: Ciba-Geigy Corporation, Ardsley, N.Y.

[ * ] Notice: The portion of the term of this patent subsequent to Jan. 21, 1992, has been disclaimed.

[22] Filed: Oct. 20, 1972

[21] Appl. No.: 299,488

[30] Foreign Application Priority Data
Oct. 21, 1971 Switzerland............... 15339/71

[52] U.S. Cl................ 260/308 R; 424/269; 424/224
[51] Int. Cl.².................................. C07D 249/12
[58] Field of Search..................... 260/308 R

[56] References Cited
FOREIGN PATENTS OR APPLICATIONS
2,057,170    5/1971   Germany............... 260/308 R OTHER PUBLICATIONS
Chemical Abstracts, Abstracting South African Patent 68/03,471, Oct. 31, 1968, Chemical Abstracts Vol. 71, Abstract 101861 (1969).

*Primary Examiner*—John D. Randolph
*Assistant Examiner*—Robert T. Bond
*Attorney, Agent, or Firm*—Harry Falber; Frederick H. Rabin

[57] ABSTRACT

Triazolylthiophosphonic esters corresponding to the formula

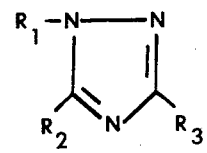

wherein $R_1$ represents a phenyl radical which is substituted by one or more fluorine, bromine and/or iodine atoms, by lower alkyl, lower alkoxy, lower alkylthio, lower trihalogenoalkyl, lower alkyl-SO, lower alkyl-$SO_2$ or $O_2N$ groups, which may be the same or different, or by at least one chlorine and at least one fluorine, bromine or iodine atom, one lower alkyl, lower alkoxy, lower alkylthio, lower trihalogenoalkyl, lower alkyl-SO, lower alkyl-$SO_2$ or $O_2N$ group, or represents an unsubstituted or halogenated and/or alkoxylated phenyl-lower alkyl radical or diphenylmethyl, and one of the symbols $R_2$ and $R_3$ represents hydrogen or a lower alkyl radical and the other represents the radical

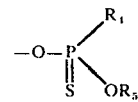

wherein $R_4$ represents a lower alkyl radical or the phenyl radical and $R_5$ represents a lower alkyl radical their manufacture and their use in pest control.

10 Claims, No Drawings

TRIAZOLYLTHIOPHOSPHORIC ACID ESTERS

The present invention relates to triazolylthiophosphonic esters, a process for their manufacture and to their use in pest control.

The triazolylthiophosphonic esters correspond to the formula

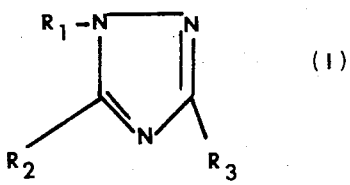

wherein $R_1$ represents a phenyl radical which is substituted by one or more fluorine, bromine and/or iodine atoms, by lower alkyl, lower alkoxy, lower alkylthio, lower trihalogenoalkyl, lower alkyl-SO, lower alkyl-$SO_2$ or $O_2N$ groups, which may be the same or different, or by at least one chlorine and at least one fluorine, bromine or iodine atom, one lower alkyl, lower alkoxy, lower alkylthio, lower trihalogenoalkyl, lower alkyl-SO, lower alkyl-$SO_2$ or $O_2N$ group, or represents an unsubstituted or halogenated and/or alkoxylated phenyl-lower alkyl radical or diphenylmethyl, and one of the symbols $R_2$ and $R_3$ represents hydrogen or a lower alkyl radical and the other represents the radical

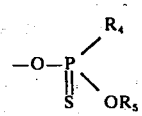

wherein $R_4$ represents a lower alkyl radical or the phenyl radical and $R_5$ represents a lower alkyl radical.

By a lower alkyl, alkoxy or alkylthio radical is meant in each case a straight-chain or branched radical containing from 1 to 5 carbon atoms, for example methyl, methoxy, methylthio, ethyl, ethoxy, ethylthio, n-propyl, propoxy, isopropyl, n-butyl and n-pentyl and isomers thereof. A phenyl-lower alkyl radical is to be understood as meaning those radicals which contain one to four, preferably one or two, carbon atoms in the side-chain. Examples of such radicals are:

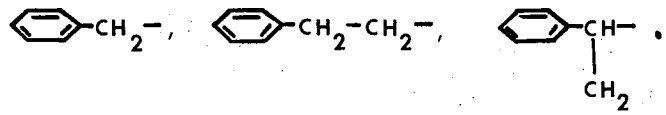

Preferred trihalogenoalkyl groups are trifluoromethyl groups. Preferred compounds on account of their activity are those of the formula I, wherein $R_1$ represents 4-methylmercaptophenyl, 4-nitrophenyl, 3-nitrophenyl, 2-trifluoromethylphenyl, 3-trifluoromethylphenyl, 3-tolyl, 4-tolyl, 2-methyl-4-chlorophenyl, $R_2$ represents hydrogen or $C_1$–$C_3$ alkyl, $R_3$ represents

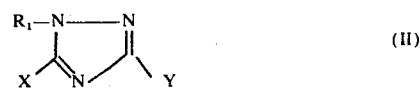

$R_4$ represents methyl, ethyl or phenyl, and $R_5$ represents $C_1$–$C_5$ alkyl.

The new triazolylthiophosphonic esters of the formula I are manufactured according to the invention by
a. reacting a hydroxy-triazole of the formula II $$R_1-N-\!\!\!-\!\!\!-N \atop X\diagdown N \diagdown Y \qquad \text{(II)}$$

in which one of the symbols X and Y represents hydrogen or a lower alkyl radical and the other represents the hydroxyl group, and $R_1$ has the meanings given for the formula I, with a thiophosphonic halide of the formula III

in which Hal represents chlorine or bromine, $R_4$ and $R_5$ have the meanings given for the formula I, in the presence of an acid binding agent, or
b. reacting a metal salt of a hydroxy-triazolyl of the formula II with a thiophosphonic halide of the formula III. As salts of hydroxytriazoles of the formula II which are suitable for the process according to the invention there may be used, for example, salts of monovalent metals, in particular the alkali metal salts; besides these, however, there may be used other salts, for example those of monovalent heavy metals.

As acid binding agents the following bases may for example be used: tertiary amines, such as triethylamine, dimethyl aniline, pyridine, inorganic bases, for examples hydroxides and carbonates of alkali and alkaline earth metals, preferably sodium and potassium carbonate.

The reactions may be carried out preferably in solvents or diluents which are inert towards the reactants. The following, for example, are suitable for this purpose: aromatic hydrocarbons, such as benzene, toluene, petroleums, halogenated hydrocarbons, chlorobenzene, polychlorobenzenes, bromobenzene, chlorinated alkanes containing 1 to 3 carbon atoms, ethers, such as dioxan, tetrahydrofuran; esters, for example ethyl acetate; ketones, for example methyl ethyl ketone, diethyl ketone, nitriles etc.

Some of the starting materials of the formula II are known compounds which can be manufactured according to methods which are known per se. These compounds are obtained for example by reacting a correspondingly substituted semi-carbazide with ortho-carboxylic acid ethyl ester, e.g. orthochloroethyl formate, or by firstly acylating a correspondingly substituted semi-carbazide and subsequently effecting cyclisation under alkaline conditions (cf. for example J. B. Chem. Ber. 56, 1797).

The compounds of the formula I have a broad biocidal activity spectrum and may be used to combat diverse plant and animal pests, for example as nematocides.

In particular, the compounds of the formula I possess insecticidal and acaricidal properties and may be used against all development stages such, for example, as eggs, larvae, pupae, nymphs and adults of insects and representatives of the order acarina, for example against insects of the families:

| | |
|---|---|
| Tettigonidae | Tenebrionidae |
| Gryllidae | Chrysomelidae |
| Gryllotalpidae | Bruchidae |
| Blattidae | Tineidae |
| Reduviidae | Noctuidae |
| Phyrrhocoriae | Lymatriidae |
| Cimicidae | Pyralidae |
| Delphacidae | Culicidae |
| Aphididae | Tipulidae |
| Diaspididae | Stomoxydae |
| Pseudococcidae | Trypetidae |
| Scarabaeidae | Muscidae |
| Dermestidae | Calliphoridae and |
| Coccinellidae | Pulicidae |

Acarida of the families:
Ixodidae
Argasidae
Tetranychidae and
Dermanyssidae.

The insecticidal and/or acaricidal action can be substantially broadened and adapted to suit the particular circumstances by the addition of other insecticides and/or acaricides.

Suitable additives include, for example, the following active substances:
Bis-O,O-diethylphosphoric acid anhydride (TEPP)
Dimethyl-(2,2,2-trichloro-1-hydroxyethyl)-phosphonate (TRICHLORFON)
1,2-dibromo-2,2-dichloroethyldimethylphosphate (NALED)
2,2-dichlorovinyldimethylphosphate (DICHLORVOS)
2-methoxycarbamyl-1-methylvinyldimethylphosphate (MEVINPHOS)
Dimethyl-1-methyl-2-(methylcarbamoyl)-vinylphosphate cis (MONOCROTOPHOS)
3-(dimethoxyphosphinyloxy)-N,N-dimethyl-cis-crotonamide (DICROTOPHOS)
2-chloro-2-diethylcarbamoyl-1-methylvinyldimethylphosphate (PHOSPHAMIDON)
O,O-diethyl-O(or S)-2-(ethylthio)-ethylthiophosphate (DEMETON)
S-ethylthioethyl-O,O-dimethyl-dithiophosphate (THIOMETON)
O,O-diethyl-S-ethylmercaptomethyldithiophosphate (PHORATE)
O,O-diethyl-S-2-ethylthio)ethyldithiophosphate (DISULFOTON)
O,O-dimethyl-S-2-(ethylsulphinyl)ethylthiophosphate (OXYDEMETON METHYL)
O,O-dimethyl-S-(1,2-dicarbethoxyethyldithiophosphate (MALATHION)
O,O,O,O-tetraethyl-S,S'-methylene-bis-dithiophosphate (ETHION)
O-ethyl-S,S-dipropyldithiophosphate
O,O-dimethyl-S-(N-methyl-N-formylcarbamoylmethyl)-dithiophosphate (FORMOTHION)
O,O-dimethyl-S-(N-methylcarbamoylmethyl)dithiophosphate (DIMETHOATE)
O,O-dimethyl-O-p-nitrophenylthiophosphate (PARATHION-METHYL)
O,O-diethyl-O-p-nitrophenylthiophosphate (PARATHION)
O-ethyl-O-p-nitrophenylphenylthiophosphate (EPN)
O,O-dimethyl-O-(4-nitro-m-tolyl)thiophosphate (FENITROTHION)
O,O-dimethyl-O-2,4-5-trichlorophenylthiophosphate (RONNEL)
O-ethyl-O,2,4,5-trichlorophenylethylthiophosphate (TRICHLORONATE)
O,O-dimethyl-O-2,5-dichloro-4-bromophenylthiophosphate (BROMOPHOS)
O,O-dimethyl-O-(2,5-dichloro-4-jodphenyl)-thiophosphate (JODOFENPHOS)
4-tert.butyl-2-chlorophenyl-N-methyl-O-methylamidophosphate (CRUFOMATE)
O,O-dimethyl-O-(3-methyl-4-methylmercaptophenyl)thiophosphate (FENTHION)
Isopropylamino-O-ethyl-O-(4-methylmercapto-3-methylphenyl)-phosphate
O,O-diethyl-O-p-(methylsulphinyl)phenyl-thiophosphate (FENSULFOTHION)
O-p-(dimethylsulphamido)phenyl-O,O-dimethylthiophosphate (FAMPHUR)
O,O,O',O'-tetramethyl-O,O'-thiodi-p-phenylenethiophosphate
O-ethyl-S-phenyl-ethyldithiophosphate
O,O-dimethyl-O-(α-methylbenzyl-3-hydroxycrotonyl)phosphate
2-chloro-1-(2,4-dichlorophenyl)vinyl-diethylphosphate (CHLORFENVINPHOS)
1-chloro-1-(2,4,5-trichlorophenyl)vinyl-dimethylphosphate
O-[2-chloro-1-(2,5-dichlorophenyl)]vinyl-O,O-diethylthiophosphate
Phenylglyoxylonitriloxim-O,O-diethylthiophosphate (PHOXIM)
O,O-diethyl-O-(3-chloro-4-methyl-2-oxo-2-H-1-benzopyran-7-yl)-thiophosphate (COUMAPHOS)
2,3-p-dioxandithiol-S,S-bis(O,O-diethyldithiophosphate) (DIOXATHION)
5-[(6-chloro-2-oxo-3-benzoxazolinyl)methyl]O,O-diethyldithio-phosphate (PHOSALONE)
2-(diethoxyphosphinylimino)-1,3-dithiolane
O,O-dimethyl-S-[2-methoxy-1,3,4-thiadiazol-5-(4H)-onyl-(4)-methyl]dithiophosphate
O,O-dimethyl-S-phthalimidomethyl-dithiophosphate (IMIDAN)
O,O-diethyl-O-(3,5,6-trichloro-2-pyridyl)thiophosphate
O,O-diethyl-O-2-pyrazinylthiophosphate (THIONAZIN)
O,O-diethyl-O-(2-isopropyl-4-methyl-6-pyrimidyl)-thiophosphate (DIAZINON)
O,O-diethyl-O-(2-chinoxalyl)thiophosphate O,O-dimethyl-S-(4-oxo-1,2,3-benzotriazin-3(4H)-ylmethyl)-dithiophosphate (AZINPHOS-METHYL)
O,O-diethyl-S-(4-oxo-1,2,3-benzotriazin-3(4H)-ylmethyl)-dithiophosphate (AZINPHOSETHYL)
S-[(4,6-diamino-s-triazin-2-yl)methyl]-O,O-dimethyldithiophosphate (MENAZON)
O,O-dimethyl-O-(3-chloro-4-nitrophenyl)thiophosphate (CHLORTHION)
O,O-dimethyl-O(or S)-2-(ethylthioethyl)thiophosphate (DEMETON-S-METHYL)
2-(O,O-dimethyl-phosphoryl-thiomethyl)-5-methoxy-pyron-4-3,4-dichlorobenzyl-triphenyl-phosphoniumchloride
O,O-diethyl-S-(2,5-dichlorophenylthiomethyl)dithiophosphate (PHENKAPTON)
O,O-diethyl-O-(4-methyl-cumarinyl-7-)-thiophosphate (POTASAN)
5-amino-bis(dimethylamido)phosphinyl-3-phenyl-1,2,4-triazole (TRIAMIPHOS)
N-methyl-5-(O,O-dimethylthiolphosphoryl)-3-thiavaleramide (VAMIDOTHION)
O,O-diethyl-O-[2-diemthylamino-4-methylpyrimidyl-(6)]-thiophosphate (DIOCTHYL)
O,O-dimethyl-S-(methylcarbamoylmethyl)-thiophosphate (OMETHOATE)
O-ethyl-O-(8-quinolinyl)-phenylthiophosphonate (OXINOTHIOPHOS)
O-methyl-S-methyl-amidothiophosphate (MONITOR)
O-methyl-O-(2,5-dichloro-4-bromophenyl)-benzothiophosphate (PHOSVEL)
O,O,O,O-tetrapropyldithiophosphate
3-(dimethoxyphosphinyloxy)-N-methyl-N-methoxy-cis-crotonamide
O,O-dimethyl-S-(N-ethylcarbamoylmethyl)dithiophosphate (ETHOATE-METHYL)
O,O-diethyl-S-(N-isopropylcarbamoylmethyl)-dithiophosphate (PROTHOATE)
S-N-(1-cyano-1-methylethyl)carbamoylmethyldiethylthiolphosphate (CYANTHOATE)
S-(2-acetamidoethyl)-0,0-dimethyldithiophosphate
Hexamethylphosphoric acid triamide (HEMPA)
O,O-dimethyl-O-(2-chloro-4-nitrophenyl)thiophosphate (DICAPTHON)
O,O-dimethyl-O-p-cyanophenyl thiophosphate (CYANOX)
O-ethyl-O-p-cyanophenylthiophosphonate
O,O-diethyl-O-2,4-dichlorophenylthiophosphate (DICHLORFENTHION)
O,2,4-dichlorophenyl-O-methylisopropylamidothiophosphate
O,O-diethyl-O-2,5-dichloro-4-bromophenylthiophosphate (BROMOPHOS-ETHYL)
Dimethyl-p-(methylthio)phenylphosphate
O,O-dimethyl-O-p-sulfamidophenylthiophosphate
O-[p-(p-chlorophenyl)azophenyl]O,O-dimethylthiophosphate (AZOTHOATE)
O-ethyl-S-4-chlorophenyl-ethyldithiophosphate
O-isobutyl-S-p-chlorophenyl-ethyldithiophosphate
O,O-dimethyl-S-p-chlorophenylthiophosphate
O,O-dimethyl-S-(p-chlorophenylthiomethyl)dithiophosphate
O,O-diethyl-p-chlorophenylmercaptomethyl-dithiophosphate (CARBOPHENOTHION)
O,O-diethyl-S-p-chlorophenylthiomethyl-thiophosphate
O,O-dimethyl-S-(carbethoxy-phenylmethyl)dithiophosphate (PHENTHOATE)
O,O-diethyl-S-(carbofluorethoxy-phenylmethyl)-dithiophosphate
O,O-dimethyl-S-carboisopropoxy-phenylmethyl)-dithiophosphate
O,O-diethyl-7-hydroxy-3,4-tetramethylene-coumarinyl-thiophosphate (COUMITHOATE)
2-methoxy-4-H-1,3,2-benzodioxaphosphorin-2-sulphide
O,O-diethyl-O-(5-phenyl-3-isooxazolyl)thiophosphate
2-(diethoxyphosphinylimino)-4-methyl-1,3-dithiolane
Tris-(2-methyl-1-aziridinyl)-phosphine oxide (METEPA)
S-(2-chloro-1-phthalimidoethyl)-O,O-diethyldithiophosphate
N-hydroxynaphthalimido-diethylphosphate
Dimethyl-3,5,6-trichloro-2-pyridylphosphate
O,O-dimethyl-O-(3,5,6-trichloro-2-pyridyl)thiophosphate
S-2-(ethylsulphonyl)ethyl dimethylthiolphosphate (DIOXYDEME-TON-S-METHYL)
Diethyl-S-2-(ethylsulphinyl)ethyl dithiophosphate (OXIDISULFOTON)
Bis-O,O-diethylthiophosphoric acid anhydride (SULFOTEP)
Dimethyl-1,3-di(carbomethoxy)-1-propen-2-yl-phosphate
Dimethyl-(2,2,2-trichloro-1-butyroyloxyethyl)phosphate (BUTONATE)
O,O-dimethyl-O-(2,2-dichloro-1-methoxy-vinyl)-phosphate
Bis-(dimethylamido)fluorphosphate (DIMEFOX)
3,4-dichlorobenzyl-triphenylphosphoniumchloride
Dimethyl-N-methoxymethylcarbamoylmethyl-dithiophosphate (FORMOCARBAM)
O,O-diethyl-O-(2,2-dichloro-1-chloroethoxyvinyl)-phosphate
O,O-dimethyl-O-(2,2-dichloro-1-chloroethoxyvinyl)phosphate
O-ethyl-S,S-diphenyldithiolphosphate
O-ethyl-S-benzyl-phenyldithiophosphonate
O,O-diethyl-S-benzyl-thiolphosphate
O,O-dimethyl-S-(4-chlorophenylthiomethyl)dithiophosphate (METHYLCARBOPHENOTHION)
O,O-dimethyl-S-(ethylthiomethyl)dithiophosphate
Diisopropylaminofluorophosphate (MIPAFOX)
O,O-dimethyl-S-(morpholinylcarbamoylmethyl)dithiophosphate (MORPHOTHION)
Bismethylamido-phenylphosphate
O,O-dimethyl-S-(benzene sulphonyl)dithiophosphate
O,O-dimethyl-(S and O)-ethylsulphinylethylthiophosphate
O,O-diethyl-O-4-nitrophenylphosphate
Triethoxy-isopropoxy-bis(thiophosphinyl)disulphide
2-methoxy-4H-1,3,2,benzodioxaphosphorin-2-oxide
Octamethylpyrophosphoramide (SCHRADAN)
Bis (dimethoxythiophospphinylsulphido)-phenylmethane
N,N,N',N'-tetramethyldiamidofluorophosphate (DIMEFOX)
O-phenyl-O-p-nitrophenyl-methanthiophosphonate (COLEP)
O-methyl-O-(2-chloro-4-tert.butyl-phenyl)-N-methylamidothiophosphate (NARLENE)

O-ethyl-O-(2,4-dichlorophenyl)-phenylthiophosphonate
O,O-diethyl-O-(4-methylmercapto-3,5-dimethylphenyl)-thiophosphate
4,4'-bis-(O,O-dimethylthiophosphoryloxy)-diphenyl disulphide
O,O-di-(β-chloroethyl)-O-(3-chloro-4-methylcoumarinyl-7)-phosphate
S-(1-phthalimidoethyl)-O,O-diethyldithiophosphate
O,O-dimethyl-O-(3-chloro-4-diethylsulphamylphenyl)-thiophosphate
O-methyl-O-(2-carbisopropoxyphenyl)-amidothiophosphate
5-(O,O-dimethylphosphoryl)-6-chloro-bicyclo(3.2.0)-heptadiene (1,5)
O-methyl-O-(2-i-propoxycarbonyl-1-methylvinyl)-ethylamido-thiophosphate.

Nitrophenols and Derivatives 4,6-dinitro-6-methylphenol, Na-salt [Dinitrocresol]
dinitrobutylphenol-(2,2',2''-triethanolamine salt
2-cyclohexyl-4,6-dinitrophenyl [Dinex]
2-(1-methylheptyl)-4,6-dinitrophenyl-crotonate [Dinocap]
2-sec.-butyl-4,6-dinitrophenyl-3-methyl-butenoate [Binapacryl]
2-sec.-butyl-4,6-dinitrophenyl-cyclopropionate
2-sec.-butyl-4,6-dinitrophenylisopropylcarbonate [Dinobuton]

Miscellaneous

Pyrethin I
Pyrethin II
3-allyl-2-methyl-4-oxo-2-cyclopentan-1-yl-chrysanthemumate (Allethrin)
6-chloriperonyl-chrysanthemumate (Barthrin)
2,4-dimethylbenzyl-chrysanthemumate (Dimethrin)
2,3,4,5-tetrahydrophthalimidomethylchrysanthemumate
4-chlorobenzyl-4-chlorophenylsulphide [Chlorobensid]
6-methyl-2-oxol, 3-Dithiolo-[4,5-b]-quinoxaline [Quinomethionate]
(I)-3-(2-furfuryl)-2-methyl-4-oxocyclopent-2-enyl-(I)-(cis+trans)-chrysanthemum-monocarboxylate [Furethrin]
2-pivaloyl-indane-1,3-dione [Pindon]
N'-(4-chloro-2-methylphenyl)-N,N-dimethylformamidine [Chlorophenamidin]
4-chlorobenzyl-4-fluorophenyl-sulphide [Fluorobenside]
5,6-dichloro-1-phenoxycarbanyl-2-trifluoromethylbenzimidazole [Fenozaflor]
p-chlorophenyl-p-chlorobenzenesulphonate [Ovex]
p-chlorophenyl-benzenesulphonate [Fenson]
p-chlorophenyl-2,4,5-trichlorophenylsulphone [Tetradifon]
p-chlorophenyl-2,4,5-trichlorophenylsulphide [Tetrasul]
p-chlorobenzyl-p-chlorophenylsulphide [Chlorobenside]
2-thio-1,3-dithiolo-(,5-6)-quinoxaline [Thiochinox]
prop-2-ynyl-(4-t-butylphenoxy)-cyclohexylsulphite [Propargil].

Formamidines 1-dimethyl-2-(2'-methyl-4'-chlorophenyl)-formamidine (CHLOR-PHENAMIDIN)
1-methyl-2-(2'-methyl-4'-chlorophenyl)-formamidine
1-methyl-2-(2'-methyl-4'-bromophenyl)-formamidine
1-methyl-2-(2',4'-dimethylphenyl)-formamidine
1-n-butyl-1-methyl-2-(2'-methyl-4'-chlorophenyl)-formamidine
1-methyl-1-(2'-methyl-4'-chloroaniline-methylene)-formamidine
2-(2''-methyl-4''-chlorophenyl)-formamidine
1-n-butyl-2-(2'-methyl-4'-chlorophenyl-imino)-pyrolidine.

Urea

N-2-methyl-4-chlorophenyl-N',N'-dimethyl-thiourea.

Carbamate 1-naphthyl-N-methylcarbamate (CARBARYL)
2-butinyl-4-chlorophenylcarbamate
4-dimethylamino-3,5-xylyl-N-methylcarbamate
4-dimethylamino-3-tolyl-N-methylcarbamate (AMINOCARB)
4-methylthio-3,5-xylyl-N-methylcarbamate (METHIOCARB)
3,4,5-trimethylphenyl-N-methylcarbamate
2-chlorophenyl-N-methylcarbamate (CPMC)
5-chloro-6-oxo-2-norborane-carbonitrile-O-(methylcarbamoyl)-oxime
1-(dimethylcarbamoyl)-5-methyl-3-pyrazolyl-N,N-dimethylcarbamate (DIMETILAN)
2,3-dihydro-2,2-dimethyl-7-benzofuranyl-N-methylcarbamate (CARBOFURAN)
2-methyl-2-methylthio-propionaldehyde-O-(methylcarbamoyl)-oxime (ALDICARB)
8-chinaldyl-N-methylcarbamate and their salts
methyl 2-isopropyl-4-(methylcarbamoyloxy)carbanilate
m-(1-ethylpropyl)phenyl-N-methylcarbamate
3,5-di-tert.butyl-N-methylcarbamate
m-(1-methylbutyl)phenyl-N-methylcarbamate
2-isopropylphenyl-N-methylcarbamate
2-sec.butylphenyl-N-methylcarbamate
m-tolyl-N-methylcarbamate
2,3-xylyl-N-methylcarbamate
3-isopropylphenyl-N-methylcarbamate
3-tert.butylphenyl-N-methylcarbamate
3-sec.butylphenyl-N-methylcarbamate
3-isopropyl-5-methylphenyl-N-methylcarbamate (PROMECARB)
3,5-diisopropylphenyl-N-methylcarbamate
2-chloro-5-isopropylphenyl-N-methylcarbamate
2-chloro-4,5-dimethylphenyl-N-methylcarbamate
2-(1,3-dioxolan-2-yl)phenyl-N-methylcarbamate (DIOXACARB)
2-(4,5-dimethyl-1,3-dioxolan-2-yl)phenyl-N-methylcarbamate
2-(1,3-dioxolan-2-yl)phenyl-N,N-dimethylcarbamate
2-(1,3-dithiolan-2-yl)-N,N-dimethylcarbamate
2-(1,3-dithiolan-2-yl)phenyl-N,N-dimethylcarbamate
2-isopropoxyphenyl-N-methylcarbamate (APROCARB)
2-(2-propinyloxy)phenyl-N-methylcarbamate
3-(2-propinyloxy)phenyl-N-methylcarbamate
2-dimethylaminophenyl-N-methylcarbamate
2-diallylaminophenyl-N-methylcarbamate 4-diallylamino-3,5-xylyl-N-methylcarbamate (ALLYXICARB)
4-benzothienyl-N-methylcarbamate
2,3-dihydro-2-methyl-7-benzofuranyl-N-methylcarbamate
3-methyl-1-phenylpyrazol-5-yl-N,N-dimethylcarbamate
1-isopropyl-3-methylpyrazol-5-yl-N,N-dimethylcarbamate (ISOLAN)
2-dimethylamino-5,6-dimethylpyrimidin-4-yl-N,N-dimethyl-carbamate
3-methyl-4-dimethylaminomethyleneiminophenyl-N-methylcarbamate
3-dimethylamino-methyleneiminophenyl-N-methylcarbamate (FORMETANATE) and their salts
1-methylthio-ethylimino-N-methylcarbamate (METHOMYL)
2-methylcarbamoyloximino-1,3-dithiolane
5-methyl-2-methylcarbamoyloximino-1,3-oxythiolane
2-(1-methoxy-2-propoxy)phenyl-N-methylcarbamate
2-(1-butin-3-yl-oxy)phenyl-N-methylcarbamate
1-dimethylcarbamyl-1-methylthio-O-methylcarbamyl-formoxime
1-(2'-cyanoethylthio)-O-methylcarbamyl-acetaldoxime
1-methylthio-O-carbamyl-acetaldoxime
O-(3-sec.butylphenyl)-N-phenylthio-N-methylcarbamate
2,5-dimethyl-1,3-dithioland-2-(O-methylcarbamyl)-aldoxime)
O-2-diphenyl-N-methylcarbamate
2-(N-methylcarbamyl-oximino)-3-chloro-bicyclo[2.2.1]heptane
2-(N-methylcarbamyl-oximino)-bicyclo[2.2.1]heptane
3-isopropylphenyl-N-methyl-N-chloroacetyl-carbamate
3-isopropylphenyl-N-methyl-N-methylthiomethyl-carbamate
O-(2,2-dimethyl-4-chloro-2,3-dihydro-7-benzofuranyl)-N-methyl-carbamate
O-(2,2,4-trimethyl-2,3-dihydro-7-benzofuranyl)-N-methylcarbamate
O-naphthyl-N-methyl-N-acetyl-carbamate
O-5,6,7,8-tetrahydronaphthyl-N-methyl-carbamate
3-isopropyl-4-methylthio-phenyl-N-methylcarbamate
3,5-dimethyl-4-methoxy-phenyl-N-methylcarbamate
3-methoxymethoxy-phenyl-N-methylcarbamate
3-allyloxyphenyl-N-methylcarbamate
2-propargyloxymethoxy-phenyl-N-methyl-carbamate
2-allyloxyphenyl-N-methyl-carbamate
4-methoxycarbonylamino-3-isopropylphenyl-N-methyl-carbamate
3,5-dimethyl-4-methoxycarbonylamino-phenyl-N-methyl-carbamate
2-γ-methylthiopropylphenyl-N-methyl-carbamate
3-(α-methoxymethyl-2-propenyl)-phenyl-N-methyl-carbamate
2-chloro-5-tert.-butyl-phenyl-N-methyl-carbamate
4-(methyl-propargylamino)-3,5-xylyl-N-methyl-carbamate
4-(methyl-γ-chloroallylamino)-3,5-xylyl-N-methyl-carbamate
4-(methyl-β-chloroallylamino)-3,5-xylyl-N-methyl-carbamate
1-(β-ethoxycarbonalethyl)-3-methyl-5-pyrazolyl-N,N-dimethyl-carbamate
3-methyl-4-(dimethylamino-methylmercapto-methyleneimino)phenyl-N-methylcarbamate
1,3-bis(carbamoylthio)-2-(N,N-dimethylamino)-propanehydrochloride
5,5-dimethylhydroresorcinoldimethylcarbamate
2-[ethyl-propargylamino]-phenyl-N-methylcarbamate
2-[methyl-propargylamino]-phenyl-N-methylcarbamate
2-[dipropargylamino]-phenyl-N-methylcarbamate
4-[dipropargylamino]-3-tolyl-N-methylcarbamate
4-[dipropargylamino]-3,5-xylyl-N-methylcarbamate
2-[allyl-isopropylamino]-phenyl-N-methylcarbamate
3-[allyl-isopropylamino]-phenyl-N-methylcarbamate Chlorinated Hydrocarbons γ-hexachlorocyclohexane [GAMMEXANE; LINDAN; γ HCH]
1,2,4,5,6,7,8,8-octachloro-3α,4,7,7α'tetrahydro-4,7-methylenindane [CHLORDAN]
1,4,5,6,7,8,8-heptachloro,3α,4,7,7α-tetrahydro-4,7-methylenindane [HEPTACHLOR]
1,2,3,4,10,10-hexachloro-1,4,4α,5,8,8α-hexahydro-endo-1,4-exo-5,8-dimethanonaphthalene [ALDRIN]
1,2,3,4,10,10-hexachloro-6,7-epoxy-1,4,4α,5,6,7,8,8α-oxta-hydro-exo-1,4-endo-5,8-dimethanonaphthalene [DIFLORIN]
1,2,3,4,10,10-hexachloro-5,7 epoxy-1,4,4α,5,6,7,8,8αocty-hydro-endo-endo-5,8-dimethanonaphthalene [ENDRIN]

The active substances of the formula I also possess excellent fungicidal properties against phytopathogenic fungi in cultivated plants of the most diverse kinds, such as cereals, maize, rice, vegetables, ornamental plants, fruit trees, grapevines, farm products etc.

Using the active substances of the invention it is possible to check or destroy fungus infections which have occured on fruit, blossoms, leaves, stems, tubers and roots, and parts of plants which then grow later also remain free from such infections. The active substances of the formula I are active against the phytopathogenic fungi belonging to the following classes, orders and species of fungi: Oomycetes, Zygomycetes, Asomycetes, Basidomycetes, Denteromycetes.

The active substances according to the invention can also be used for treating seed grain, fruit, tubers etc. and for protecting then from fungus infections, for example from smut fungi of all kinds, such as:

Ustilaginales, such as Ustilago types (*Ustilago avenae*)
Tilletia types (*Tilletia tritici*),
Urocystis and Tuburcinia types
Phoma types (*Phoma betae*).

To broaden their activity spectrum the active substances of the formula I may contain in admixture bactericides, fungistatic agents, bacteriostatic agents, nematocides, and/or, for example, the following fungicides:

dodecylquanidine acetate (DODINE)
pentachloronitrobenzene (QUINTOZENE)
pentachlorophenol (PCP)
2-(1-methyl-n-propyl)-4,6-dinitrophenyl-2-methylcrotonate (BINAPACRYL)
2-(1-methyl-n-heptyl)-4,6-dinitrophenylcrotonate (DINOCAP)

2,6-dichloro-4-nitroaniline (DICHLORAN)
2,3,5,6-tetrachloro-benzoquinone (1,4) (CHLORANIL)
2,3-dichloro-naphthoquinone (1,4) (DICHLONE)
N-(trichloromethylthio) phthalimide (FOLPAT)
N-(trichloromethylthio) cyclohex-4-en-1,2-dicarboximide (CAPTAN)
N-(1,1,2,2-tetrachloroethylthio)cyclohex-4-en-1,2-dicarboximide (CAPTAFOL)
N-methansulfonal-N-trichloromethylthio-chloroaniline
N'-dichlorofluoromethylthio-N,N-dimethyl-N'-phenylsulfamide (DICHLOFLUANID)
O-ethyl-S-benzyl-phenyldithiophosphate
O,O-diethyl-S-benzyl-thiolphosphate
disodium-ethylene-1,2-bis-dithiocarbamate (NABAM)
zinc-ethylene-1,2-bis-dithiocarbamate (ZINEB)
manganese-ethylene-1,2-bis-dithiocarbamate (polymeric) (MANEB)
tetramethylthiuramdisulfide (THIRAM)
1-oxy-3-acetyl-6-methyl-cyclohexane-(5)dione-(2,4) (DEHYDRO-ACETIC ACID)
8-hydroxyquinoline (8-QUINOLINOL)
2-dimethylamino-6-methyl-5-n-butyl-4-hydroxy-pyrimidine
methyl-N-benzimidazole-2-yl-N-(butylcarbamoyl)-carbamate (BENOMYL)
2-ethylamino-6-methyl-5n-butyl-4-hydroxypyrimidine
2,3-dicyano-1,4-dithia-anthraquinone (DITHIANON)
2-(4-thiazolyl)-benzimidazole
3,5-dimethyltetrahydro-1,3,5-thiadiazine-2-thione (DAZOMET)
2,3-dihydro-5-carboxanilido-6-methyl-1,4-oxathine
pentachlorobenzyl alcohol.

Furthermore, the new compounds of the formula I possess extraordinarily good nematocidal properties and may be used to combat, for example, plant pathogenic nematodes.

The compounds of the formula I may be used as pure active substance or together with suitable carriers and/or additives. Suitable carriers and additives can be solid or liquid and correspond to the substances conventionally used in formulation techniques such, for example, as solvents dispersants, wetting agents, adhesives, thickeners, binders and/or fertilisers.

For application, the compounds of the formula I may be processed to dusts, emulsion concentrates, granules, dispersions, sprays, to solutions, or suspensions in the conventional formulation which is commonly employed in application terminology. Mention may also be made of "cattle dips" and "spray races", in which aqueous preparations are used.

The agents according to the invention are manufactured in known manner by intimately mixing and/or grinding active substances of the formula I with the suitable carriers, optionally with the addition of dispersants or solvents which are inert towards the active substances. The active substances may be available and can be used in the following forms:
Solid forms
Dusts, tracking agents, granules, coated granules, impregnated granules and homogeneouos granules.
Liquid forms:
a. active substances which are dispersible in water: wettable powders, pastes, emulsions;
b. solutions.

To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminum silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used alone or in admixture with one another.

Granules can be very easily manufactured by dissolving an active substance of the formula I in an organic solvent and applying the resulting solution to a granulated material, for example attapulgite, $SIO_2$, granicalcium, bentonite etc. and then evaporating the solvent.

Polymer granules can also be manufactured by mixing the active substances of the formula I with polymerizable compounds (urea/formaldehyde; dicyandiamide/formaldehyde; melamine/formaldehyde or others), whereupon a mild polymerisation is carried out that does not affect the active substances and in the process of which the granulation is carried out during the gel formation. It is more advantageous to impregnate finished, porous polymer granules (urea/formaldehyde, polyacrylonitrile, polyester or others) which have a specific surface area and a favourable predeterminable adsorption/desorption ratio, with the active substances, for example in the form of their solutions (in a low boiling solvent) and to remove the solvent. Polymer granules of this kind in the form of microgranules having a bulk density of 300 g/liter to 600 g/liter can also be manufactured with the aid of atomisers. The dusting can be carried out from aircraft over extensive areas of cultures of useful plants.

It is also possible to obtain granules by compacting the carrier with the active substance and carriers and subsequently comminuting the product.

To these mixtures can also be added additives which stabilize the active substance and/or non-ionic, anionic and cationic surface active substances, which for example improve the adhesion of the active ingredients on plants or parts of plants (adhesives and agglutinants) and/or ensure a better wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per moecule and 8 to 9 carbon atoms in the alkyl radical, lignin sulfonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active substance, i.e. wettable powders, pastes and emulsifiable concentrates, are agents which can be diluted with water to any concentration desired. They consist of active substance, carrier, optionally additives which stabilize the active substance, surface-active substance and anti-foam agents and, optionally, solvents.

Wettable powders and pastes are obtained by mixing and grinding the active substances with dispersing agents and pulverulent carriers in suitable apparatus until homogeneity is attained. Carriers are, for example, those mentioned for the solid forms of application. In some cases it is advantageous to use mixtures of different carriers. As dispersing agents there can be used, for example, condensation products of sulfonated naphthalene and sulfonated naphthalene derivatives with formaldehyde, condensation products of naphthalene or naphthalene sulfonic acids with phenol and formaldehyde, as well as alkali, ammonium and alkaline earth metal salts of lignin sulfonic acid, in addition, alkylaryl sulfonates, alkali and alkaline earth metal salts of dibutyl naphthalene sulfonic acid, fatty alcohol sulfates such as salts of sulfated hexadecanols, heptadecanols, octadecanols, and salts of sulfated fatty alcohol glycol ethers, the sodium salt of oleoyl ethionate, the sodium salt of oleoyl methyl tauride, ditertiary acetylene glycols, dialkyl dilauryl ammonium chloride and fatty acid alkali and alkaline earth metal salts.

Suitable anti-foam agents are silicones.

The active substances are mixed, ground, sieved and strained with the additives mentioned above that, in wettable powder, the solid particle size of from 0.02 to 0.04 and in pasts, of 0.03 is not exceeded. To produce emulsifiable concentrates and pastes, dispersing agents such as those cited above, organic solvents and water are used. Examples of suitable solvents are the following: alcohols, benzene, xylenes, toluene, dimethyl sulfoxide, and mineral oil fractions boiling between 120° and 350° C. The solvents must be not phytotoxic, inert to the active substances.

Furthermore, the agents according to the invention can be applied in the form of solutions. For this purpose the active substance or several active substances of the general formula I are dissolved in suitable organic solvents, mixtures of solvents or in water. Aliphatic and aromatic hydrocarbons, chlorinated derivatives thereof, alkyl naphthalenes, and mineral oils alone or mixed with each other, can be used as organic solvents.

The content of active substance in the above described agents is between 0.1% to 95%, in which connection it should be mentioned that in the case of application from aircraft or some other suitable means of application, it is possible to use concentrations of up to 99.5% or even pure active substance.

The active substances of the formula I can, for example, be formulated as follows:

Dusts

The following substances are used to manufacture (a) a 5% and (b) a 2% dust:
a. 5 parts of active substance   95 parts of talcum
b. 2 parts of active substance   1 part of highly disperse silica   97 parts of talcum.
The active substances are mixed with the carriers and ground.

Granules

The following substances are used to produce 5% granules:
5 parts of active substance
0.25 parts of epichlorohydrin
0.25 parts of cetyl polyglycol ether
3.50 parts of polyethylene glycol
91 parts of kaolin (particle size 0.3-0.8 mm).
The active substance is mixed with epichlorohydrin and dissolved with 6 parts of acetone; the polyethylene glycol and cetyl polyglycol ether are then added. The thus obtained solution is sprayed on to kaolin, and the acetone subsequently evaporated in vacuo.

Wettable powder

The following constituents are used for the preparation of (a) a 40%, (b) and (c) a 25%, and (d) a 10% wettable powder:
a. 40 parts of active substance   5 parts of sodium lignin sulphonate   1 part of sodium dibutyl-naphthalene sulphonate   54 parts of silica acid.
b. 25 parts of active substance   4.5 parts of calcium lignin sulphonate   1.9 parts of Champagne chalk/hydroxyethyl cellulose mixture (1:1)   1.5 parts of sodium dibutyl naphthalene sulphate   19.5 parts of silica acid   19.5 parts of Champagne chalk   28.1 parts of kaolin.
c. 25 parts of active substance   2.5 parts of isooctylphenoxy-polyoxyethylene-ethanol   1.7 parts of Champagne chalk/hydroxyethyl cellulose mixture (1:1)   8.3 parts of sodium aluminum silicate   16.5 parts of kieselgur   46 parts of kaolin.
d. 10 parts of active substance   5 parts of naphthalenesulphonic acid/formaldehyde condensate   82 parts of kaolin.

The active substances are intimately mixed, in suitable mixers, with the additives, the mixture being then ground in the appropriate mills and rollers. Wettable powder are obtained which can be diluted with water to give suspensions of any desired concentration.

Emulsifiable concentrates

The following substances are used to produce (a) a 10% and (b) a 25% emulsifiable concentrate:
a. 10 parts of active substance   3.4 parts of epoxidised vegetable oil   13.4 parts of a combination emulsifier consisting of fatty alcohol polyglycol ether and alkylarylsulphonate calcium salt   40 parts of dimethylformamide   43.2 parts of xylene.
b. 25 parts of active substance   2.5 parts of epoxidised vegetable oil   10 parts of an alkylarylsulphonate/fatty alcohol-polyglycol ether mixture   5 parts of dimethylformamide   57–5 parts of xylene.

From these concentrates it is possible to produce, by dilution with water, emulsion of any desired concentration.

Spray

The following constituents are used to prepare a 5% spray:
5 parts of active substance
1 part of epichlorohydrin
94 parts of benzene. (boiling limits 160°–190°C).

EXAMPLE 1

21.0 g (0.1 M) of 1-(4-chloro-2-methylphenyl)-3-hydroxy-1,2,4-triazole (m.p. 22°–21°C) and 13.8 g (0.1 M) of potassium carbonate are boiled under reflux for 2 hours in 250 ml of methyl ethyl ketone. The solution is cooled to room temperature and 17.3 g (0.1 M) of O-ethyl-ethylthiophosphonic chloride are added dropwise to the suspension over the course of 15 minutes. The mixture is heated for 1½ hours under reflux and then stirred overnight at room temperature. The salts are filtered off and the clear filtrate is concentrated in vacuo. The residue is taken up in isopropanol and the product is crystallised by cooling the solution in a dry ice/acetone bath. The crystallised product is filtered off and dried for 15 hours in vacuo at 30°C/15 mm to give the compound of the formula

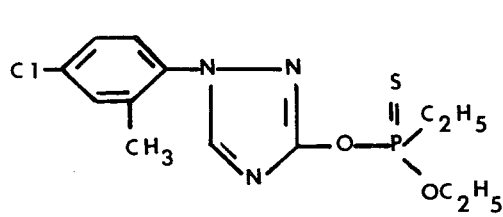

with a melting point of 62°–64°C.

The following compounds are manufactured analogously:

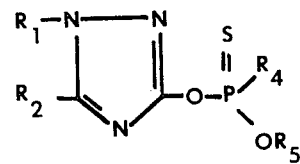

| $R_1$ | $R_2$ | $R_4$ | $R_5$ | Physical Data |
|---|---|---|---|---|
| —CH$_2$—C$_6$H$_5$ | H | —C$_2$H$_5$ | —C$_2$H$_5$ | $n_D^{20}$ = 1,5407 |
| —CH(CH$_3$)—C$_6$H$_5$ | H | —C$_2$H$_5$ | —C$_2$H$_5$ | $n_D^{20}$ = 1,5387 |
| —CH(C$_6$H$_5$)$_2$ | H | —C$_2$H$_5$ | —C$_2$H$_5$ | $n_D^{20}$ = 1,5732 |
| —C$_6$H$_4$—F | H | —C$_2$H$_5$ | —C$_2$H$_5$ | mp.: 40–43°C |
| —C$_6$H$_4$—F | —CH$_3$ | —C$_2$H$_5$ | —C$_2$H$_5$ | $n_D^{20}$ = 1,5413 |
| —C$_6$H$_4$—Br | —CH$_3$ | —C$_2$H$_5$ | —C$_2$H$_5$ | $n_D^{20}$ = 1,5471 |
| —C$_6$H$_4$—CH$_3$ | H | —C$_6$H$_5$ | —C$_2$H$_5$ | mp.: 67–70°C |
| —C$_6$H$_4$—CH$_3$ | —CH$_3$ | —C$_2$H$_5$ | —C$_2$H$_5$ | $n_D^{20}$ =1,5516 |
| —C$_6$H$_4$—CF$_3$ | H | —CH$_3$ | —C$_3$H$_{7(n)}$ | mp.: 64–66°C |
| —C$_6$H$_4$—CF$_3$ | H | —C$_2$H$_5$ | —C$_2$H$_5$ | mp.: 52–54°C |
| —C$_6$H$_4$—CF$_3$ | —CH$_3$ | —C$_2$H$_5$ | —C$_2$H$_5$ | |
| —C$_6$H$_4$—NO$_2$ | H | —C$_2$H$_5$ | —C$_2$H$_5$ | mp.: 65–70°C |
| —C$_6$H$_4$—NO$_2$ | H | —C$_2$H$_5$ | —C$_2$H$_5$ | mp.: 74–79°C |
| —C$_6$H$_4$—NO$_2$ | H | —C$_2$H$_5$ | —C$_2$H$_5$ | mp.: 96–98°C |
| —C$_6$H$_3$(CF$_3$)(Cl) | —C$_3$H$_{7(n)}$ | H | —CH$_3$ | mp.: 65–69°C |

| R₁ | R₂ | R₄ | R₅ | Physical Data |
|---|---|---|---|---|
| 4-CF₃, 3-Cl phenyl | H | —CH₃ | —C₃H₇₍ₙ₎ | mp.: 47–49°C |
| 4-CF₃ phenyl | H | —CH₃ | —C₂H₅ | mp.: 69–74°C |
| 2-CF₃ phenyl | H | —C₂H₅ | —C₂H₅ | |
| 3-CF₃ phenyl | H | —CH₃ | —C₃H₇₍ₙ₎ | |
| 2-CF₂Cl phenyl | H | —C₂H₅ | —C₂H₅ | |
| 3-CF₃, 4-Cl phenyl | H | —C₂H₅ | —C₂H₅ | |
| 3-CF₃ phenyl | H | —C₂H₅ | —CH₃ | |

EXAMPLE 2

Action against ticks

A. *Rhipicephalus bursa*

& Adult ticks or 50 tick larvae were counted into a glass tube and immersed for 1 to 2 minutes in 2 ml of an aqueous emulsion from an emulsion series each containing 100, 10, 1 and 0.1 ppm of test substance. The tube was then sealed with a standardised cotton wool plug and placed on its head, so that the cotton wool was able to absorb the active substance emulsion.

In the case of the adults evaluation took place after 2 weeks, and in that of the larvae after 2 days. Each test was repeated twice.

The compounds according to Example 1 act in the above test against adults and larvae of Rhipicephalus bursa.

B. *Boophilus microplus* (larvae)

Tests are carried out in each case with 20 sensitive and OP-resistant larvae using an analogous dilution series as in the case of test A. (The resistance relates to the tolerability of diazinone).

The compounds according to Example 1 act in the above tests against adults and larvae of Rhicephalus bursa and sensitive and OP-resistant larvae of Boophilus microplus.

EXAMPLE 3

Acaricidal action

*Phaseolus vulgaris* (dwarf beans) have an infested piece of leaf from a mass culture of Tetranychus urticae placed on them 12 hours before the test for the acaricidal action. The mobile stages which have migrated are sprayed with the emulsified test preparations from a chromatography atomiser so that the spray broth does not run off. The number of living and dead larvae, adults and eggs are evaluated after 2 to 7 days under a stereoscopic microscope and the result expressed in percentages. During the "interim", the treated plants are kept in greenhouse compartments at 25°C.

The compounds according to Example 1 are active in the above test against eggs, larvae and adults of Tetranychus urticae.

EXAMPLE 4

A. Insecticidal ingest poison action

Tobacco and potato plants are sprayed with a 0.05% aqueous emulsion (obtained from a 10% emulsifiable concentrate).

After the coating has dried, Egyptian cotton leaf worms (Spodoptera literalis) are settled on the tobacco plants and Colarado potato beetle larvae (Leptinotarsa decemlineata) on the potato plants. The test is carried out at 24°C and 60% relative humidity. In the above test the compounds according to Example 1 displayed ingest poison action against *spodoptera litoralis* and *leptinotarsa decemlineata*.

We claim:

1. A compound of the formula

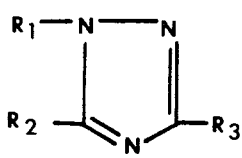

wherein $R_1$ represents a phenyl radical which is substituted by one or two fluorine or iodine atoms, by lower alkyl, lower alkoxy, lower alkylthio, trihalogeno-lower alkyl, lower alkyl-SO, lower alkyl-SO$_2$ or O$_2$N groups, which may be the same or different, or by one chlorine and one fluorine, bromine or iodine atom, one lower alkyl, lower alkoxy, lower alkylthio, trihalogeno-lower alkyl, lower alkyl-SO, lower alkyl-SO$_2$ or O$_2$N group, or represents an unsubstituted or halogenated or lower alkoxylated phenyl-lower alkyl radical or diphenylmethyl, $R_2$ represents hydrogen or a lower alkyl radical and $R_3$ represents the radical

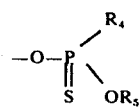

wherein $R_4$ represents a lower alkyl radical or the phenyl radical and $R_5$ represents a lower alkyl radical.

2. A compound according to claim 1, wherein $R_1$ represents 4-methylmercaptophenyl, 4-nitrophenyl, 3-nitrophenyl, 2-trifluoromethylphenyl, 3-trifluoromethylphenyl, 3-tolyl, 4-tolyl, 2-methyl-4-chlorophenyl, $R_2$ represents hydrogen or $C_1$–$C_3$ alkyl, $R_3$ represents $$-O-\underset{\underset{S}{\parallel}}{P}\diagdown\begin{matrix}R_4\\OR_5\end{matrix}$$

$R_4$ represents methyl, ethyl or phenyl, and $R_5$ represents $C_1$–$C_5$ alkyl.

3. The compound according to claim 2 of the formula

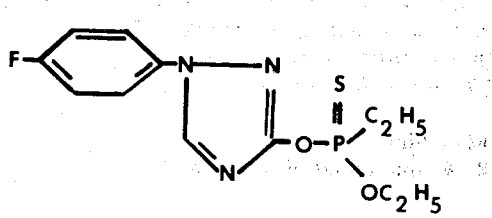

4. The compound according to claim 2 of the formula

5. The compound according to claim 2 of the formula

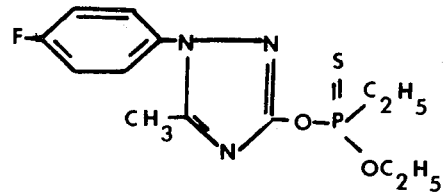

6. The compound according to claim 2 of the formula

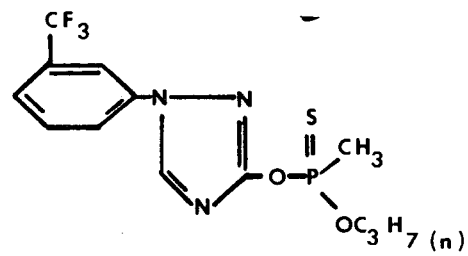

7. The compound according to claim 2 of the formula

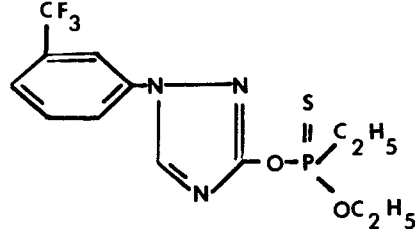

8. The compound according to claim 2 of the formula

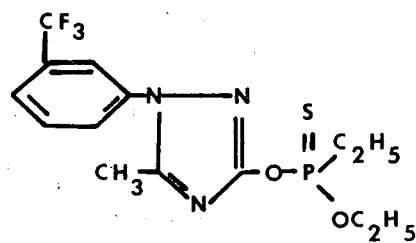

9. The compound according to claim 2 of the formula

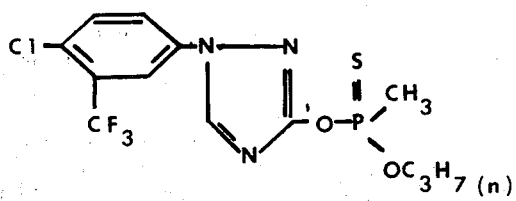

10. The compound according to claim 2 of the formula

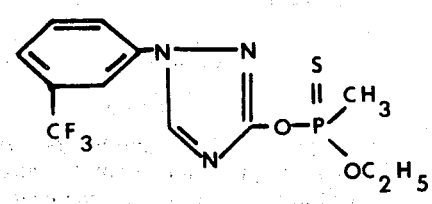

* * * * *

UNITED STATES PATENT AND TRADEMARK OFFICE
CERTIFICATE OF CORRECTION

PATENT NO. : 3,956,306
DATED : May 11, 1976
INVENTOR(S) : Dag Dawes and Beat Boehner It is certified that error appears in the above-identified patent and that said Letters Patent are hereby corrected as shown below:

Title page, item [30], add the following:

July 27, 1972 Switzerland................11231/72

Signed and Sealed this

Twenty-sixth Day of October 1976

[SEAL]

Attest:

RUTH C. MASON
*Attesting Officer*

C. MARSHALL DANN
*Commissioner of Patents and Trademarks*